(12) United States Patent  
Davis et al.

(10) Patent No.: US 9,198,560 B2
(45) Date of Patent: Dec. 1, 2015

(54) MEDICAL DIAGNOSTIC INSTRUMENT

(71) Applicant: Welch Allyn, Inc., Skaneateles Falls, NY (US)

(72) Inventors: Peter J. Davis, Skaneateles, NY (US); Ervin Goldfain, Syracuse, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 340 days.

(21) Appl. No.: 13/841,848

(22) Filed: Mar. 15, 2013

(65) Prior Publication Data

US 2013/0267783 A1   Oct. 10, 2013

Related U.S. Application Data

(60) Provisional application No. 61/612,622, filed on Mar. 19, 2012.

(51) Int. Cl.
| | |
|---|---|
| *A61B 1/00* | (2006.01) |
| *A61B 1/227* | (2006.01) |
| *A61B 3/10* | (2006.01) |
| *A61B 3/00* | (2006.01) |
| A61B 1/303 | (2006.01) |
| A61B 1/31 | (2006.01) |
| A61B 1/233 | (2006.01) |

(52) U.S. Cl.
CPC ......... *A61B 1/00188* (2013.01); *A61B 1/00052* (2013.01); *A61B 1/00195* (2013.01); *A61B 1/227* (2013.01); *A61B 3/0041* (2013.01); *A61B 3/10* (2013.01); *A61B 1/233* (2013.01); *A61B 1/303* (2013.01); *A61B 1/31* (2013.01)

(58) Field of Classification Search
CPC ........ A61B 1/227; A61B 1/233; A61B 1/303; A61B 3/12; A61B 3/1208; A61B 3/1216
USPC .......................................................... 600/200
See application file for complete search history.

(56) References Cited

U.S. PATENT DOCUMENTS

| | | | | |
|---|---|---|---|---|
| 1,515,771 A | * | 11/1924 | Greenwald | 600/200 |
| 2,843,112 A | | 7/1958 | Miller | |
| 3,373,737 A | * | 3/1968 | Connors et al. | 600/200 |
| 3,384,076 A | * | 5/1968 | Speelman | 600/200 |

(Continued)

FOREIGN PATENT DOCUMENTS

DE   20 2005 009 189 U1   10/2005

OTHER PUBLICATIONS

Focusing screen; http://en.wikipedia.org/wiki/Focusing_screen; 2 pages.

(Continued)

*Primary Examiner* — Christian Sevilla
*Assistant Examiner* — Eric S Gibson

(57) ABSTRACT

A medical diagnostic instrument that enables optical viewing of a target area, includes an optical system disposed within an instrument housing, the optical system including at least one primary optical element disposed along an optical axis. A focusing screen is distally aligned along the optical axis for focusing an image of the target area received from the optical system. The focusing screen enables a user to view the target area without requiring an eyepiece, thereby permitting the caregiver to conduct examinations without requiring intimate contact between the patient and the caregiver.

17 Claims, 10 Drawing Sheets

(56) References Cited

U.S. PATENT DOCUMENTS

| | | | | |
|---|---|---|---|---|
| 3,698,387 | A * | 10/1972 | Moore et al. | 600/200 |
| 3,978,850 | A * | 9/1976 | Moore et al. | 600/200 |
| 4,147,163 | A * | 4/1979 | Newman et al. | 600/200 |
| 4,157,216 | A | 6/1979 | Plummer | |
| 4,336,989 | A | 6/1982 | Matsumura et al. | |
| 4,380,998 | A * | 4/1983 | Kieffer et al. | 600/200 |
| 4,567,881 | A * | 2/1986 | Heller | 600/200 |
| 4,643,171 | A * | 2/1987 | Riester | 600/200 |
| 4,913,132 | A * | 4/1990 | Gabriel | 600/200 |
| 5,658,235 | A * | 8/1997 | Priest et al. | 600/112 |
| 5,733,029 | A * | 3/1998 | Monroe | 362/572 |
| 5,919,130 | A * | 7/1999 | Monroe et al. | 600/200 |
| 5,976,076 | A | 11/1999 | Kolff et al. | |
| 6,079,830 | A * | 6/2000 | Kohayakawa | 351/211 |
| 6,097,892 | A | 8/2000 | Saito | |
| 6,142,934 | A * | 11/2000 | Lagerway et al. | 600/200 |
| 6,152,873 | A * | 11/2000 | Rogers | 600/200 |
| 6,383,133 | B1 * | 5/2002 | Jones | 600/200 |
| 6,511,420 | B1 * | 1/2003 | Farrell et al. | 600/167 |
| 6,682,478 | B2 | 1/2004 | Nakamura | |
| 7,276,025 | B2 * | 10/2007 | Roberts et al. | 600/249 |
| 7,354,399 | B2 * | 4/2008 | Strom et al. | 600/200 |
| 7,399,275 | B2 | 7/2008 | Goldfain et al. | |
| 7,419,467 | B2 * | 9/2008 | Tsai | 600/109 |
| 7,803,110 | B2 * | 9/2010 | Goldfain et al. | 600/200 |
| 7,946,981 | B1 * | 5/2011 | Cubb | 600/194 |
| 8,062,216 | B2 * | 11/2011 | Raghuprasad | 600/200 |
| 8,066,634 | B2 * | 11/2011 | Andreassen et al. | 600/200 |
| 8,491,470 | B1 * | 7/2013 | Wageneck et al. | 600/200 |
| 8,543,192 | B2 * | 9/2013 | Goldfain et al. | 600/476 |
| RE44,806 | E * | 3/2014 | Roberts et al. | 315/205 |
| 2002/0038076 | A1 * | 3/2002 | Sheehan et al. | 600/200 |
| 2003/0171655 | A1 * | 9/2003 | Newman et al. | 600/200 |
| 2004/0039251 | A1 * | 2/2004 | Roberts et al. | 600/178 |
| 2004/0127771 | A1 * | 7/2004 | Heine et al. | 600/200 |
| 2004/0186352 | A1 * | 9/2004 | Roberts et al. | 600/200 |
| 2005/0027169 | A1 * | 2/2005 | Goldfain et al. | 600/200 |
| 2005/0043591 | A1 * | 2/2005 | Witte | 600/200 |
| 2005/0171399 | A1 * | 8/2005 | Rich et al. | 600/112 |
| 2010/0191063 | A1 * | 7/2010 | Hsu | 600/200 |
| 2010/0317924 | A1 * | 12/2010 | Sisko et al. | 600/200 |
| 2011/0060191 | A1 * | 3/2011 | Lynn et al. | 600/200 |
| 2011/0087073 | A1 * | 4/2011 | Huang | 600/200 |
| 2011/0166421 | A1 * | 7/2011 | Katiraei | 600/200 |
| 2012/0002422 | A1 * | 1/2012 | Lia et al. | 362/294 |
| 2013/0267783 | A1 * | 10/2013 | Davis et al. | 600/200 |

OTHER PUBLICATIONS

Jedmed All-N1 Video Otoscope; Instructions for Use; Copyright 2011; Jedmed Instrument Company; 10 pages.

Dr. Mom Otoscopes; http://www.drmomotoscope.com/faq.htm; 1 page.

ADC 5210—Standard 2.5v Diagnostic Set; http://www.southpointesurgical.com/adc_diagnostic_sets.aspx; 3 pages.

* cited by examiner

MEDICAL DIAGNOSTIC INSTRUMENT

CROSS REFERENCE TO RELATED APPLICATION

This application claims priority to U.S. Ser. No. 61/612,622, filed Mar. 19, 2012, pursuant to relevant paragraphs of 35 USC §119, the entire contents of which are herein incorporated by reference.

TECHNICAL FIELD

The subject matter described herein pertains generally to the field of diagnostic medicine and more particularly to an optical medical diagnostic instrument that enables adequate viewing of a target area of interest without recourse to an existing eyepiece.

BACKGROUND

Otoscopes are examples of diagnostic instruments commonly available to medical practitioners and caregivers for purposes of conducting a comprehensive patient examination. More specifically, otoscopes typically utilize a contained light source, such as an incandescent bulb or LED, which emits light through a distal insertion portion of an instrument head that is secured onto a handle portion of the instrument. A disposable speculum tip element is attached in releasable fashion to the exterior of the distal insertion portion, the tip element being insertable to a predetermined distance within the ear canal of the patient. A user then views the ear canal and tympanic membrane of the patient, as illuminated by the contained light source, through an eyepiece which is disposed at the proximal end of the instrument head.

Certain versions of otoscopes further include optical systems that are provided within the instrument head to better enable visualization of the target. These otoscopes also include an eyepiece at the proximal end of the instrument head to enable viewing.

Additionally, there are also known digital or electronic instrument versions that utilize an electronic imaging assembly contained within or proximate to the instrument head in order to obtain a digitized image that can be displayed or otherwise viewed in lieu of an eyepiece, either at the instrument or remotely, such as through use of a display. Though attendant to the above problem, these latter designs are relatively complex and considerably more expensive than their optical instrument counterparts.

In the case of known non-digital diagnostic instruments and particularly those having optical systems, useful visualization of the target requires that the user place their eye directly at the eyepiece portion of the instrument, therefore requiring the caregiver to be stationed extremely close to the patient. Caregivers and patients may each encounter comfort and/or convenience issues based on the acute level of proximity between the caregiver and the patient. This latter problem is not only encountered with users of otoscopes, but is also commonly experienced by users of other portable or hand-held medical diagnostic instruments.

As noted above, there are also presently available digital or electronic otoscope versions utilizing a contained electronic imager that receives the image signals from a target of interest. The received image can be transmitted to a computer, an instrument display and/or other apparatus such as a mobile computing device. As noted, however, these diagnostic instruments are considerably more expensive than their optical device counterparts. As a result, there is a general need in the field of diagnostic medicine to provide an optical diagnostic instrument that enables adequate viewing of a target area of interest, but without requiring intimate contact between the patient and the caregiver.

SUMMARY

Therefore and according to one aspect, there is provided an otoscope comprising an instrument head. An optical system is disposed within the interior of the instrument head, the optical system including at least two lens elements aligned along an optical axis for receiving an image from within the ear of a patient. A focusing screen disposed along the optical axis and proximally relative to the optical system receives a focused image from the optical system, wherein the focusing screen presents the image to a user in a format that permits viewing of the target without close proximity between the eye of the user and the instrument.

According to at least one version, at least one magnification lens element can be disposed in relation to the focusing screen. According to one version, the at least one magnification lens element is positioned proximally relative to the focusing screen and can be attached or attachable in relation to the instrument head to permit enhanced viewing of the target.

In one version, the otoscope can further include a focusing mechanism in order to shift the position of at least one of the elements of the optical system, including the focusing screen, relative to one another. In one version, the focusing screen is attached to a rotary member that enables axial movement along the optical axis.

According to another aspect, a distal insertion portion of the otoscope receives an axisymmetric tip element that permits insertion to a predetermined distance into the ear canal of a patient, at least one of the lens elements of the contained optical system being disposed within said distal insertion portion, said optical system defining an entrance pupil proximal to the distal end of said tip element and distal relative to the distal most lens element of said optical system to permit the entire tympanic membrane of a patient to be captured all at once by the optical system for focusing onto said focusing screen.

The otoscope can include an illumination source such as an incandescent bulb or at least one LED, such as a white LED. The contained focusing screen can be made from a section of a suitable optically transmissive plastic and/or ground glass.

According to yet another aspect, there is provided a portable medical diagnostic instrument, the diagnostic instrument comprising an instrument housing and an optical system disposed within the instrument housing, and in which the optical system includes at least one lens element disposed along an optical axis. A focusing screen is positioned along the optical axis proximately from the optical system for focusing an image of the target received from the optical system and enabling a user to view a target of interest at a remote distance away from the focusing screen.

According to at least one version, the diagnostic instrument can include at least one magnification lens element aligned along the optical axis and proximally relative to the focusing screen. According to one version, the at least one magnification lens element can be disposed at the rear or proximal end of the instrument housing.

The diagnostic instrument can be selected from one of the group consisting of at least one of an otoscope, a vagiscope, an anoscope, a skin surface microscope, a rhinoscope and an ophthalmoscope.

According to one version, the diagnostic instrument can further include a focusing mechanism for selectively changing the relative position of at least one component of the optical system. For example, the focusing mechanism can be configured to move the focusing screen to correspond with the changed focal position of the optical system based on, for example, the caregiver's ability to optically focus images.

One advantage provided by the herein described diagnostic instrument is that of a cost-effective alternative to existing digitized medical diagnostic instruments. Another advantage provided is that the caregiver is no longer required to maintain intimate contact with an eyepiece of the instrument while being able to adequately view and examine a target of interest using an optically based instrument without any lapses in accuracy or reliability.

Other features and advantages will be readily apparent from the following Detailed Description, which should be read in conjunction with the accompanying drawings.

DETAILED DESCRIPTION

The following describes exemplary embodiments relating to a specific (i.e., otoscope) medical diagnostic instrument. It will be readily apparent, however, that the inventive features discussed herein may be equally applicable to other medical apparatus that can be used for at least one aspect of a comprehensive patient examination. In addition, several terms are used throughout this discussion in order to provide a suitable framework in regard to the accompanying drawings, including "front", "back", "distal", "proximal", "upper", "lower" and the like. These terms are not intended, however, to be limiting with regard to the scope of the claims, except where so specifically indicated. In addition, it should be noted that the accompanying drawings are intended to illustrate aspects of medical diagnostic instruments. In that regard, these drawings are not necessarily drawn to scale.

Figure 1:
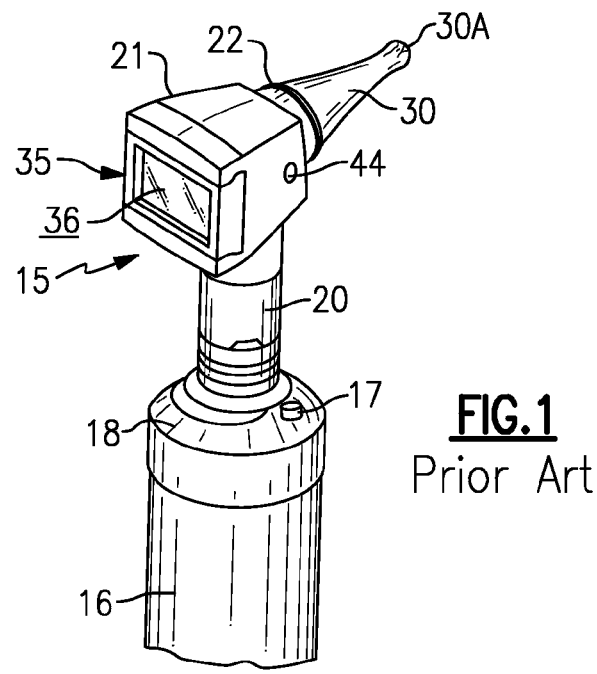
FIG. 1 is a partial rear perspective view of a known medical diagnostic instrument.
Figure 2:
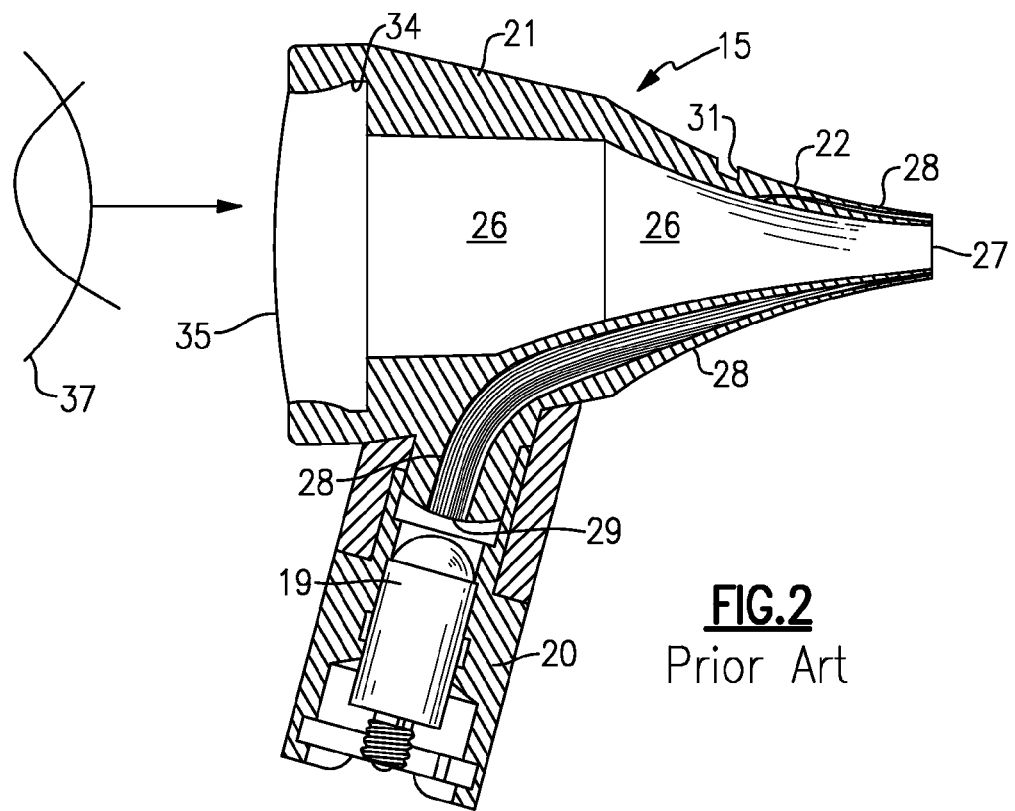
FIG. 2 depicts a side sectioned elevational view of the medical diagnostic instrument of FIG. 1.

In order to provide suitable background, reference is first made to FIGS. 1 and 2, depicting one version of a known otoscope 15. The otoscope 15 is defined by a handle 16 (only partially shown in this view) and an instrument head 21, the instrument head being attachable to the upper end of the handle 16 via an intermediate necked portion 20. The handle 16 of the otoscope 15 is substantially hollow and retains a set of stacked batteries (not shown) used for portably powering an incandescent light bulb 19 retained in the necked portion 20 of the otoscope 15 adjacent the upper end of the handle 16, and in relation to a bundle of optical fibers 28. The proximal end 29 of the optical fiber bundle 28 is polished and arranged to be optically coupled to the incandescent light bulb 19, wherein light is transmitted along the fibers to a distal end thereof, the fibers being circumferentially disposed about the distal end 27 of an insertion section 22 of the instrument head 21. A rheostat 18 is used to control the amount of illumination provided for viewing, the rheostat 18 being disposed on an upper portion of the handle 16 along with an actuation button 17. The instrument head 21, including the insertion section 22, is defined by a substantially hollow interior 26, which is sealed, including an insufflation port 44 extending laterally from one side of the instrument head 21.

The proximal portion of the instrument head 21 includes an eyepiece 35, which is stationarily fitted within an opening or cavity 34 that is formed at the rear of the instrument head 21 in order to enable viewing of the target (i.e., ear canal and tympanic membrane (TM)) through the interior 26 of the instrument head 21. The distal insertion section 22 is substantially frusto-conical in terms of its configuration and includes an exterior slot 31 that enables a hollow speculum tip element 30, FIG. 1, to be releasably attached thereto using a bayonet-type attachment. Other tip elements can be utilized, such as those described in U.S. Pat. No. 7,399,275B2, incorporated by reference herein in its entirety.

In operation, the entire instrument 15 is portable and enables the user to maintain hand-held operation throughout the course of a diagnostic examination. More specifically and to conduct an examination, the speculum tip element 30, which is preferably molded from plastic and disposable, includes an interior feature (not shown) that enables releasable attachment in bayonet-like fashion to a slot 31, FIG. 2, onto the distal insertion section 22 of the instrument head 21, as shown only in FIG. 1. The speculum tip element 30 is also substantially frusto-conical in terms of its configuration and is defined by respective and concentrically disposed distal and proximal tip openings. The distal tip opening 30(a) is shown in FIG. 1, the speculum tip element 30 being designed to be positioned only to a predetermined distance within the ear canal of the patient in order to prevent injury. The attached tip element 30 is then positioned within the ear canal (not shown) of the patient and the user (not shown) places their eye 37 at the eyepiece 35 to enable viewing of the target area.

To provide additional background, a second known version of an otoscope 60 is partially depicted in FIGS. 3-9. According to this version, an instrument head 64 retains an optical system 90 comprising an imaging lens train 94 as well as an eyepiece mechanism 100. The imaging lens train 94 extends from an distal axisymmetric insertion portion 70 of the instrument head 64 along a defined optical axis 92 and includes a plurality of optical components. The majority of these optical components are retained within an open-ended tubular member 98 made up of three (3) adjacent axial sections wherein each axial section is defined by a different interior diameter. The first axial section 102 of the tubular member 98, defined at its distal end, is sized for retaining an objective distal or front lens 112 and an adjacent lens 116, these lenses forming a doublet. The lenses 112, 116 are mounted such that the objective lens 112 partially extends outwardly from the distal most opening of the tubular member 98. The adjacent second axial section 106 of the tubular member 98 is defined by a second interior diameter that is larger than that of the first axial section 102, this section linking an adjacent third axial section 110 that contains a first relay lens 117, an aperture plate or stop 120 and a second relay lens 124, respectively, each of these optical elements being appropriately spaced from one another. The interior diameter of the third axial section 110 is larger than those of each of the first and second axial sections 102, 106 of the tubular member 98.

Figure 3:
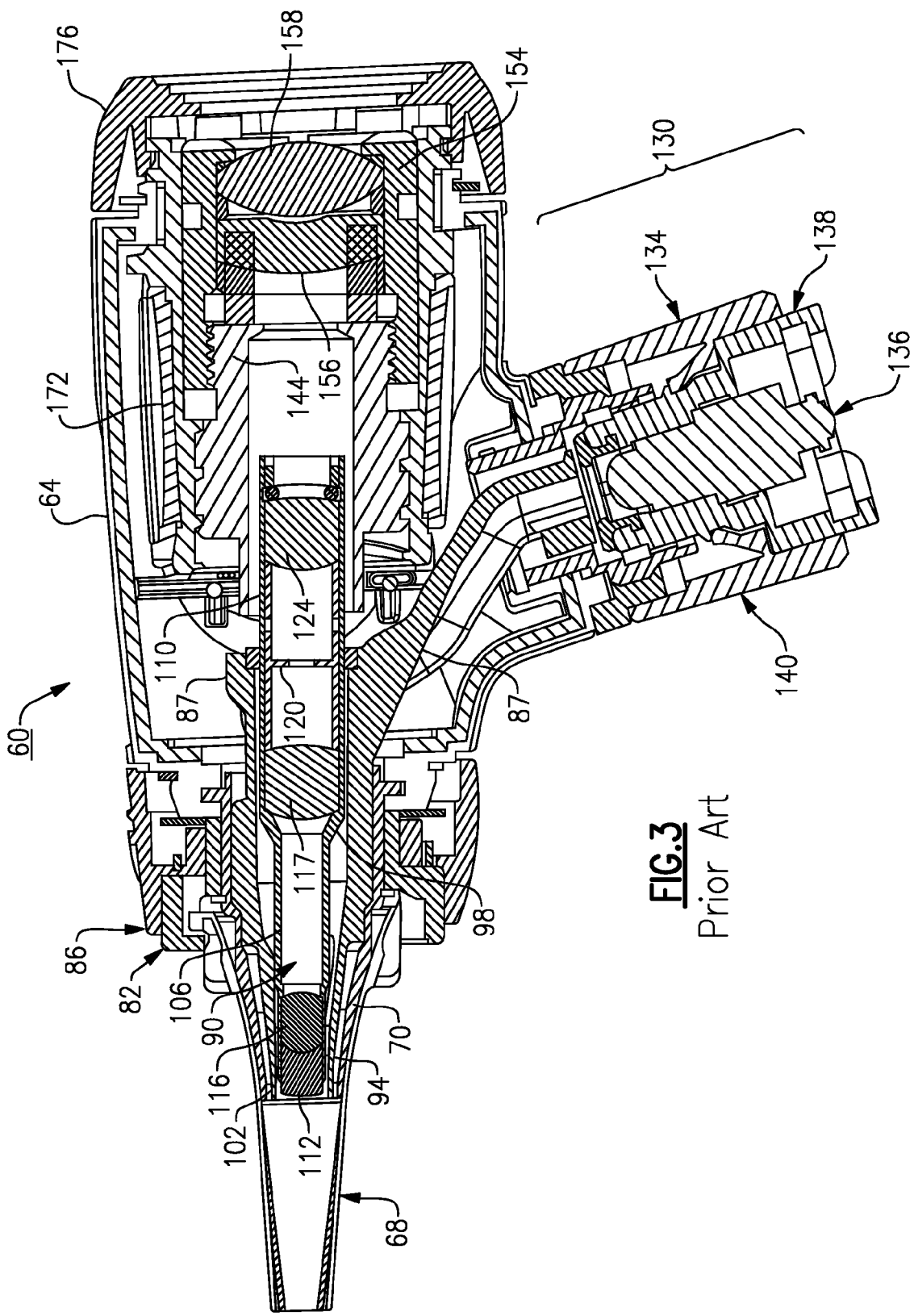
FIG. 3 is a side sectioned elevational view of another known medical diagnostic instrument.

As shown in FIG. 3, the tubular member 98 is retained within a structural inner former assembly 87 of the instrument head 84 such that the first axial section 102 of the tubular member 98 is positioned within the hollow interior of the distal axisymmetric insertion portion 70. The inner former assembly 87 provides support for the tubular member 98 and further provides means for supporting a plurality of optical fibers (not shown) from an illumination assembly 130 that is fitted within a necked portion 134 of the herein described instrument 60. The illumination assembly 130 includes a miniature incandescent bulb 136 mounted within a base 138 and retained within a cylindrical sleeve member 140. The illumination assembly 130 is electrically connected via an adjustable rheostat (not shown) to a set of batteries (not shown) retained within the handle (not shown) of the instrument 60.

Figure 4:
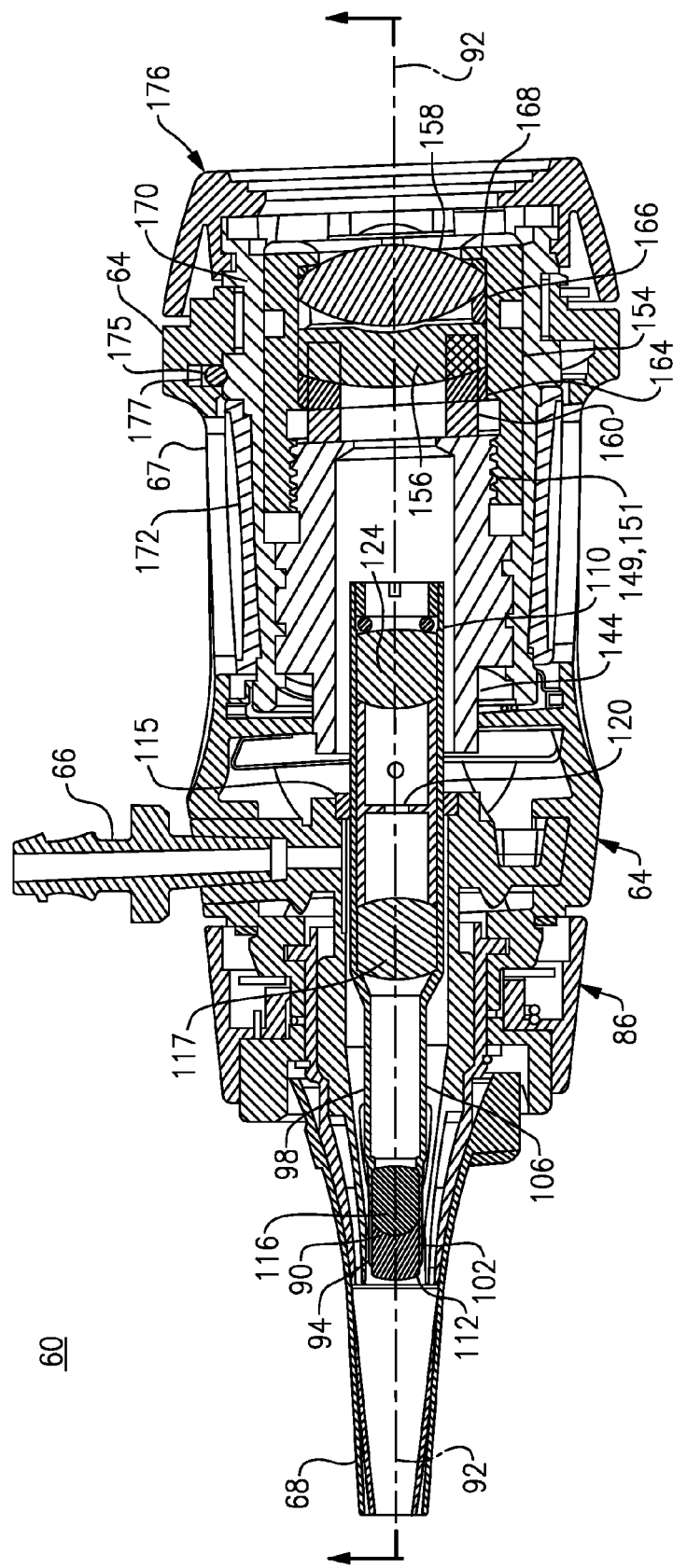
FIG. 4 is a top sectional view of the medical diagnostic instrument of FIG. 3.

Referring to FIGS. 3 and 4, the first axial section 102 of the tubular member 98 is fitted within the distal axisymmetric portion 70 of the instrument head 64 such that the distal objective lens 112 is proximate the distal opening thereof and wherein a seal 115 is provided for the tubular member relative to the inner former assembly 87, the third axial section 110 of the tubular member extending proximally therefrom. The above seal is preferred in those instances in which the instrument 60 is to be used for pneumatic otoscopy, including an insufflation port 66 extending from one side of the instrument head 64.

Figure 5:
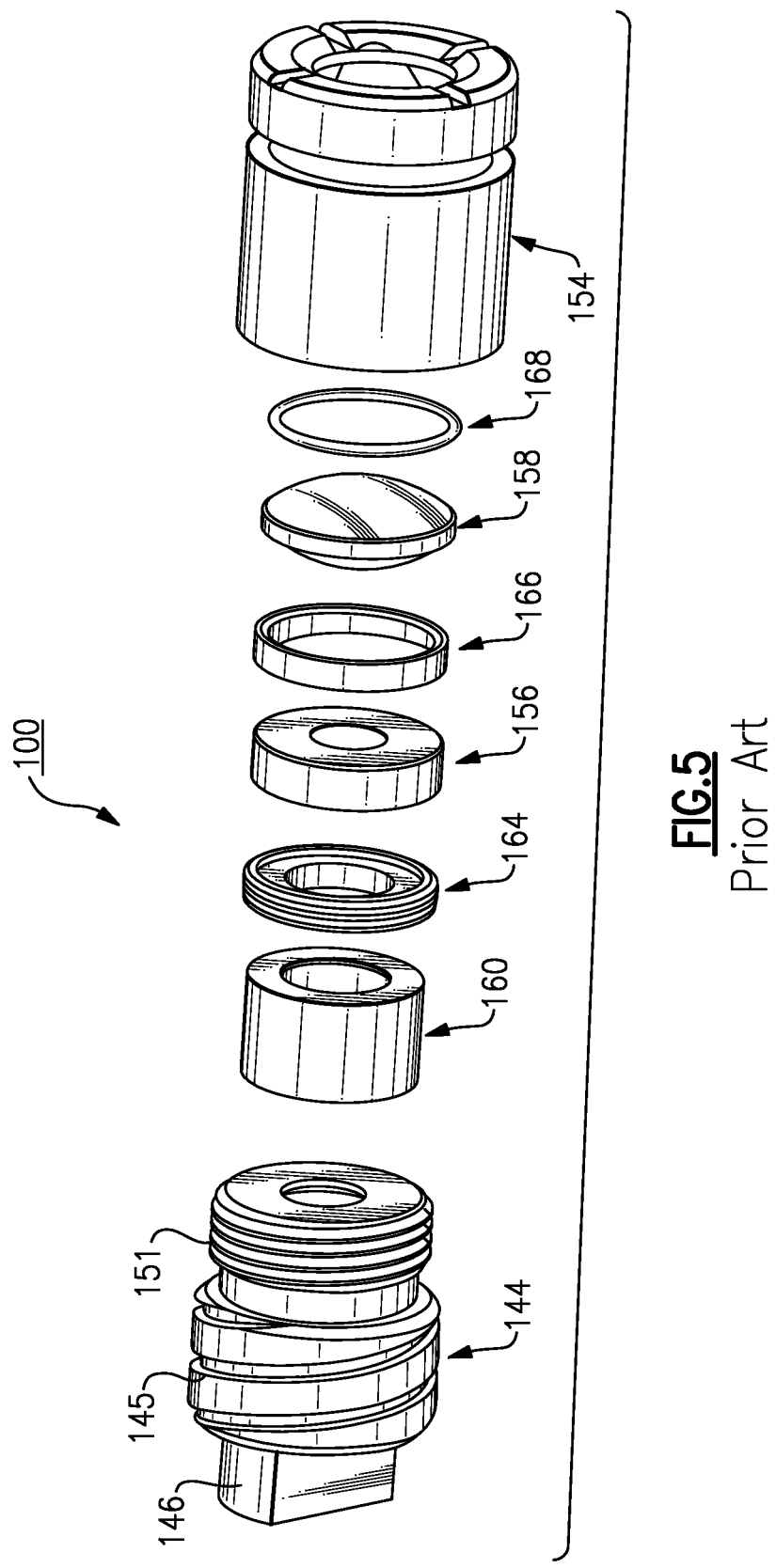
FIG. 5 is an exploded view of the eyepiece mechanism of the diagnostic instrument of FIGS. 3 and 4.
Figure 6:
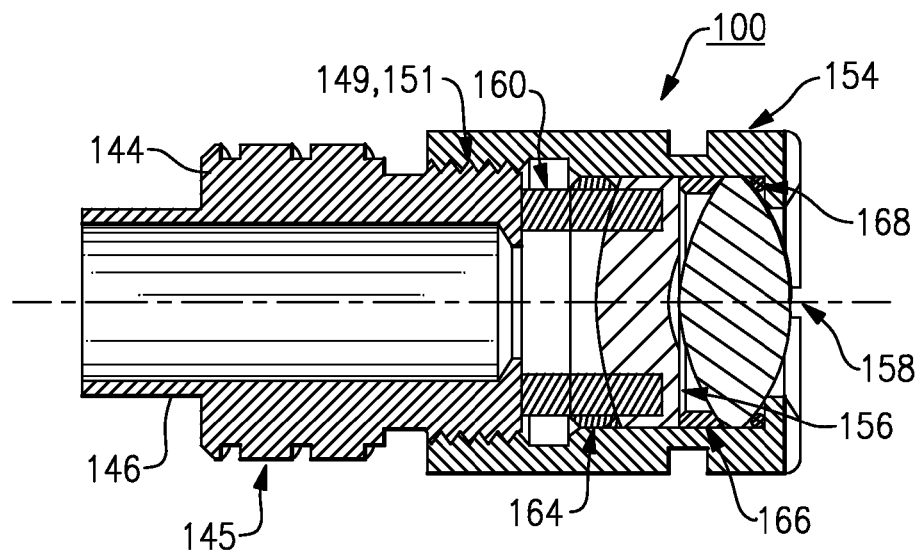
FIG. 6 is a side sectional view of the eyepiece mechanism of FIG. 5 in assembled form.

Referring to FIGS. 4-6 and as previously noted, the optical system 90 of the herein described instrument 60 further includes an eyepiece mechanism 100 that is retained at the proximal end of the instrument head 64. The eyepiece mechanism 100 includes a substantially cylindrical lens carrier member 144 having a set of external threads 145 that are disposed adjacent to a square distal end 146 thereof. The square distal end 146 of the lens carrier member 144 is sized to be fitted into a corresponding opening (not shown) provided within the interior of the instrument head 64 that retains the lens carrier member and prevents same from rotational movement. A tubular lens retainer member 154 is fixedly attached to the lens carrier member 144 by means of respective threaded portions 149, 151 provided on the interior distal end of the lens retainer member and the exterior of the lens carrier member. The lens retainer member 154 is defined by an interior sized for receiving a pair of optical lenses 156, 158 that, when the lens retainer member and lens carrier member 144 are assembled to the instrument head 64, are aligned along the optical axis 92 with the imaging lens train. A wave spring 160 and lens retainer 164 are disposed between the lens 156 and lens carrier member 144 and a spacer 166 is disposed between the lenses 156, 158. An O-ring 168 is used to seal the lens 158 with the lens retainer member 154.

Figure 7:
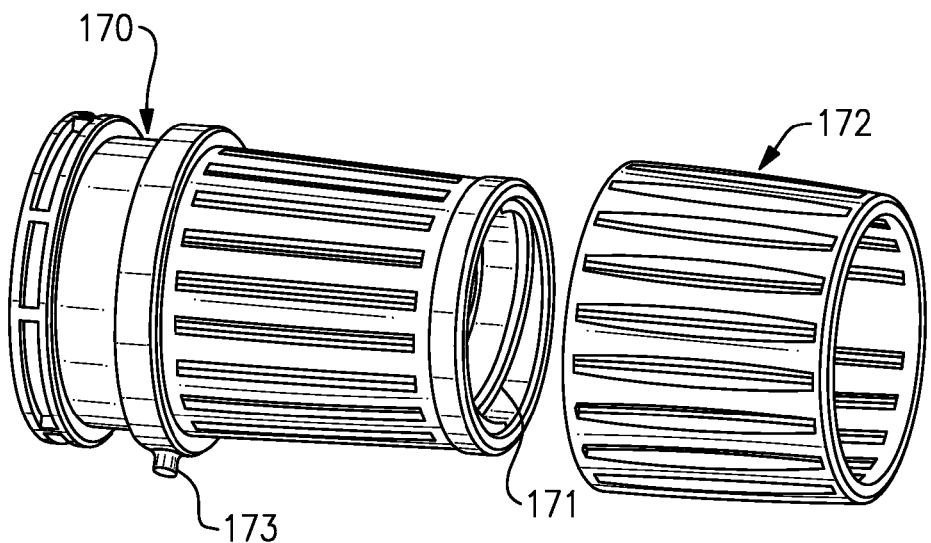
FIG. 7 is a exploded assembly view of a focusing sleeve portion of the diagnostic instrument of FIGS. 3-6.
Figure 8:
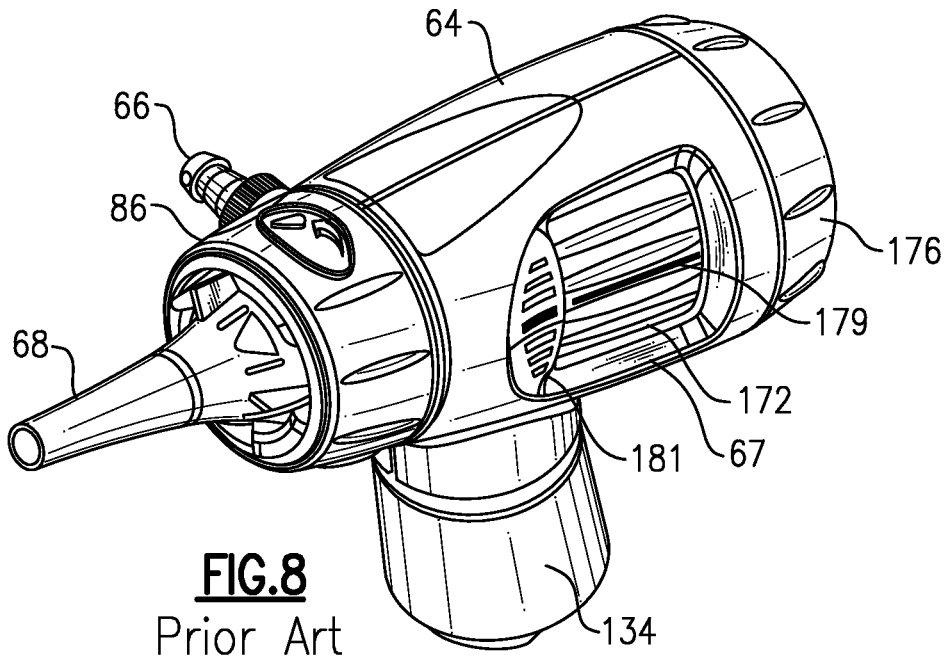
FIGS. 8 and 9 are perspective views of a portion of the medical diagnostic instrument of FIGS. 3-7.
Figure 9:
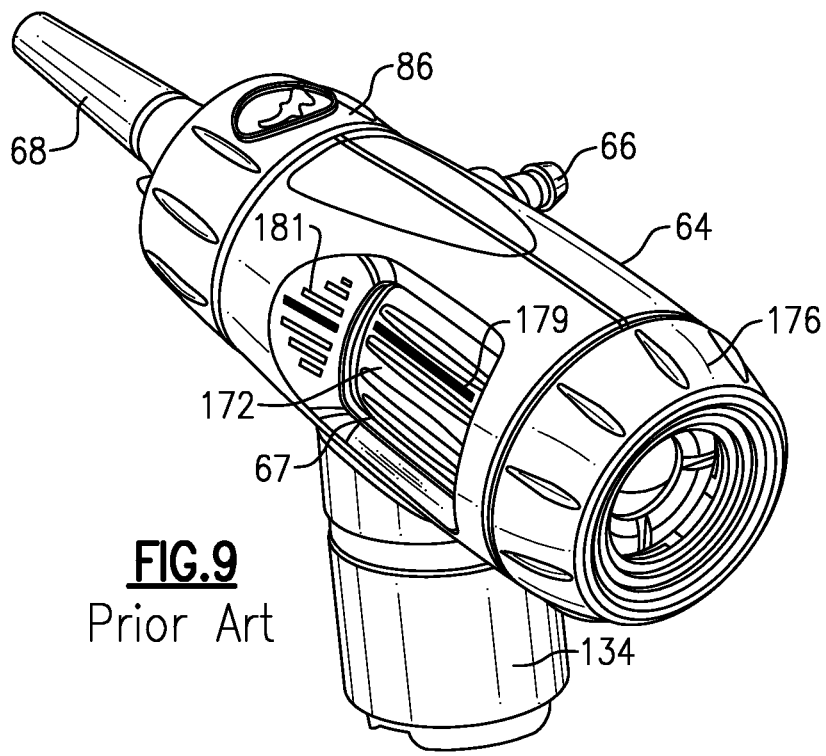

Referring to FIGS. 4-7, the external threads 145 of the lens carrier member 144 engage corresponding threads 171 formed on the interior surface of a cylindrical focusing sleeve member 170 that is fitting in overlaying relation. The focusing sleeve member 170 has an axial length that projects from the proximal end of the instrument head 64 when the sleeve member 170 is attached. Referring to FIGS. 4 and 7, a soft grippable elastomeric cover 172 overlays a portion of the sleeve member 170, the cover being mounted to permit rotation along with the sleeve member to an end of travel as determined by a protrusion 173, FIG. 7. As most clearly shown in FIG. 4, a ball 175 and compression spring 177 are each disposed within the interior of the instrument head 64, each being aligned with a single depression that is formed on the exterior of the focusing sleeve member 170, the spring biasing the ball and forming a rotational detent that signals to the user that predetermined factory-set focus position has been reached. A focusing knob 176 is snap-fitted onto the extending proximal end of the focusing sleeve member 170. The focusing knob 176, lens carrier member 144 and focusing sleeve member 170 are each defined by a center opening aligned with one another, permitting the user to view a target along the aligned optical axis 92. Axial adjustment of the eyepiece mechanism 100 is enabled relative to the imaging lens train portion of the optical system of the instrument 60 through rotational movement of the sleeve member 170. Preferably and during assembly, the lens retainer member 154 is adjusted relative to the lens carrier member 144 in order to create a factory setting, for example, for human patients at a certain focal length and a longer focal length, for example, in veterinary uses, and in which the sleeve member 170 is adjustable either above or below this position.

For purposes of adjustability, the instrument head 64 further includes a pair of windows 67 that are formed on opposing lateral sides. Axial portions of the soft grippable elastomeric cover 172 are accessible to the user through these windows 67 in addition to the focusing knob 176. Respective indicator sections 179, 181 are optionally provided on the soft elastomeric cover 172 and adjacent to the windows 67 in order to permit a predetermined focusing position, such as a nominal focus position. Further details relating to the preceding features are provided in cross-referenced U.S. Pat. No. 7,399,275 B2, the entire contents of which are incorporated in their entirety.

Referring to FIGS. 3, 4, 8 and 9, the herein described otoscope 60 further includes a tip actuator mechanism that permits a hollow speculum tip element 68 to be releasably attached to the distal axisymmetric insertion portion 70 of the instrument head 64. More specifically, the tip actuator mechanism includes a retaining member 82 fixedly attached at the distal end of the instrument head 64, the retaining member including a series of annular circumferential securing slots (not shown). An actuator knob 86 is rotatably attached to the retaining member 82. The hollow speculum tip element 68, which is fabricated from a moldable plastic and is disposable, is defined by distal and proximal tip openings and includes three (3) external engagement features in the form of ramped or stepped surfaces molded or otherwise formed at a proximal end of the tip element. Two of the annular engagement slots formed in the retaining member 82 include engagement features that correspond with and engage corresponding exterior engagement features of a mounted tip element 68. A third engagement slot, however, is empty and does not include a corresponding engagement feature. The actuator knob 86 includes a pin feature (not shown) that enters the third engagement slot when the knob is rotated in a specific direction engaging the external engagement feature of the tip element in order to selectively release the hollow speculum tip element 68 from the otoscope 60. As noted, additional details to any of the preceding features involving the instrument described in FIGS. 3-9, including but not limited to the focusing mechanism, the tip element and tip actuator mechanism are described in cross-referenced U.S. Pat. No. 7,399,275 B2.

Referring to FIGS. 3, 4, 8 and 9, the optical system 90 is aligned with the end openings of the tip element 68 to permit viewing of the ear canal and tympanic membrane in which the optical system 90, and more specifically the aperture stop 120, creates an entrance pupil that is formed distal to the distal most optical element (objective lens 112) of the optical system 90, but proximal to the distal opening of an attached tip element 68 in order to prevent vignetting. Using this configuration, the entire tympanic membrane can be viewed all at once through the eyepiece mechanism 100 of the herein described instrument 60.

Figure 10:
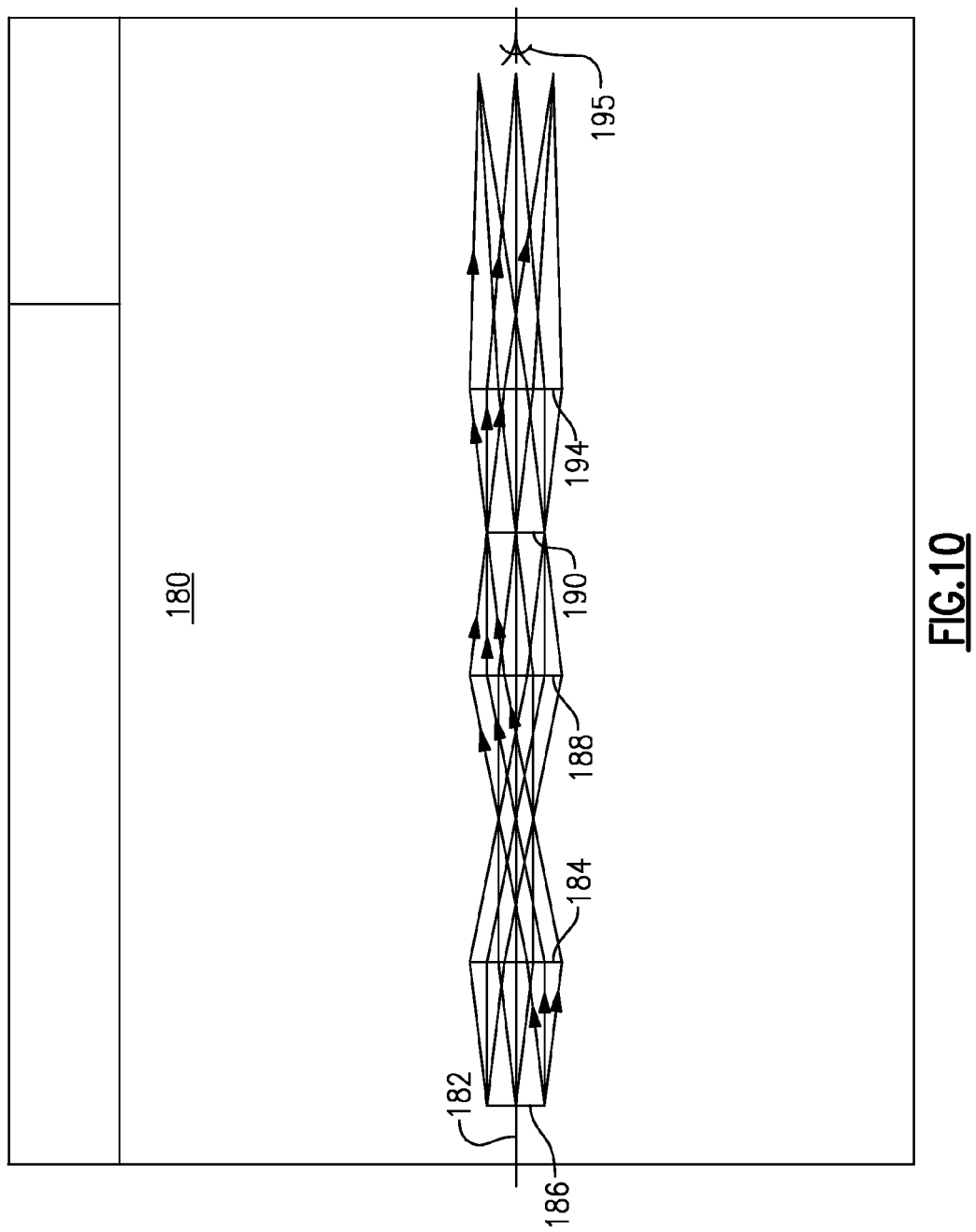
FIG. 10 is a diagrammatic view of an optical system for use in a medical diagnostic instrument and according to an exemplary embodiment.

With the preceding background and referring now to FIG. 10, there is shown a diagrammatic ray-trace view of an optical system 180 that is made in accordance with an exemplary embodiment. According to this embodiment, the optical system 180 comprises a series of optical elements that are each disposed and spaced from one another along a defined optical axis 182. More specifically, an objective lens 184 is positioned at the distal end of the optical system 180 wherein an image from a target plane 186 of interest is initially obtained and inverted. At least one additional lens element 188 is positioned proximally to the objective lens 184 along the optical axis 182 that restores the orientation of the target plane image, which is then transmitted to a focusing screen 190, the latter component also being disposed proximally along the optical axis 182 relative to each of the prior optical components. For purposes of this discussion, the focusing screen 190 is a section formed from ground glass or a suitable optically transmissive plastic that is appropriately sized and configured axially in relation to the above optical components to receive the focused image of the target. According to this configuration, a magnification lens element 194 is additionally positioned along the optical axis 182, proximal to the focusing screen 190, the magnification lens element enabling an enhanced (e.g., 2×-10×) focused image of the target to be seen without requiring the user to place their eye 195 in close proximity with an eyepiece of the instrument.

Figure 11:
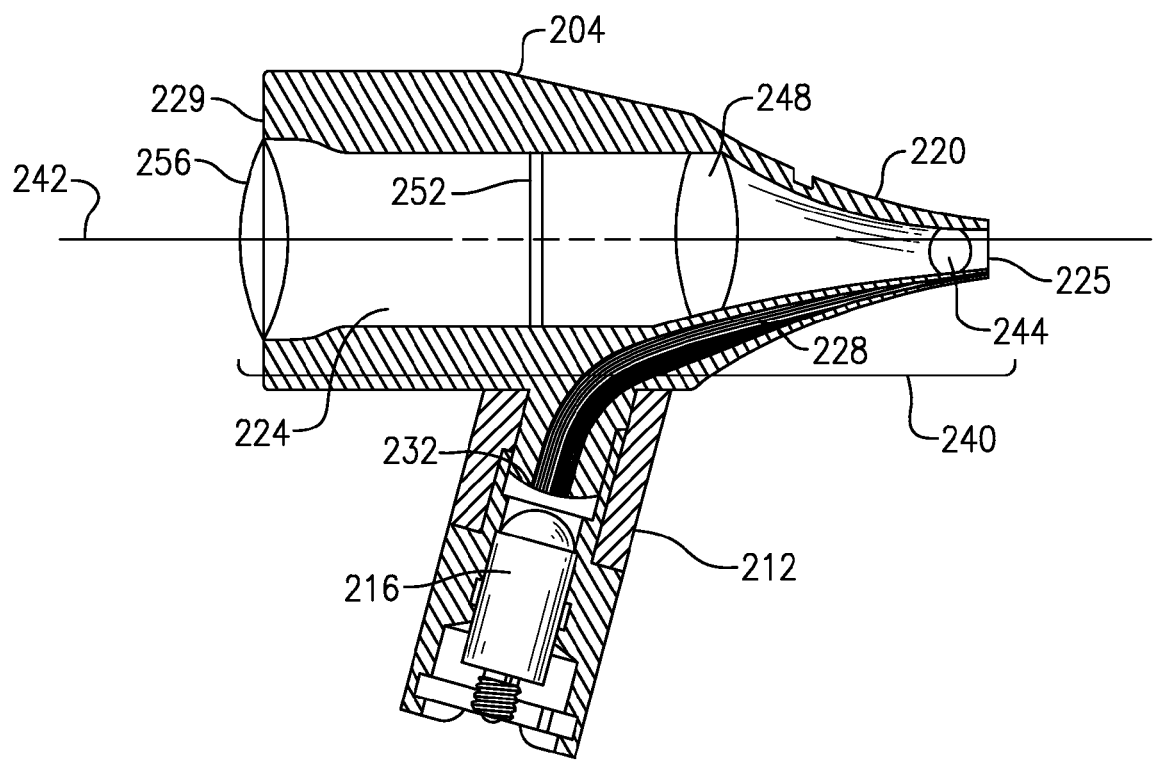
FIG. 11 is a side sectioned elevational view of a medical diagnostic instrument in accordance with a first embodiment.

With reference to FIG. 11, there is shown an otoscopic instrument 200 that has been configured with the optical system of FIG. 10. The otoscopic instrument 200 includes an instrument head 204 that is secured to an intermediate necked portion 212 of a handle (not shown), the latter containing batteries (not shown) for powering an illumination source 216; for example, a miniature incandescent light bulb or an LED, such as a white LED. A plurality of optical fibers 228 having a polished proximal end 232 guides illumination from the source 216 to a distal end of the instrument 200 and more particularly towards the distal opening 225 of an axisymmetric insertion portion 220. The insertion portion 220 is defined by a truncated substantially frusto-conical configuration, which is further configured to releasably retain a disposable speculum tip element (not shown) for insertion into the ear canal of a patient.

An optical system 240 similar to that described in FIG. 10 is disposed within the hollow interior 224 of the instrument head 204 of the otoscope 200. This optical system 240 includes an objective lens 244, which according to this embodiment is supported within the interior of the distal axisymmetric insertion portion 220 and in relation to a second lens 248, each of the lenses being aligned along an optical axis 242 that is further aligned with the distal opening 225 of the axisymmetric insertion portion 220. The lenses 244, 248 can be fixedly mounted within at least one lens tube (not shown) in which the lenses can be disposed either within or outside the insertion portion 220. Alternatively, the lenses 244, 248 can be mounted within the instrument head 204 for relative movement therebetween.

A focusing screen 252 is disposed at the focal plane of the optical system 240, the focusing screen also being arranged along the optical axis 242. The focusing screen 252 is an appropriately sized section of ground glass or an optically transmissive plastic. Finally, a magnification lens element 256 is retained at the proximal end 229 of the instrument head 204, the magnification lens element also being aligned along the optical axis 242. The optical axis 242 is substantially aligned with the center of the distal open end 225 of the axisymmetric insertion portion 220 and the cavity at the proximal end 229 of the instrument head 204 supporting the magnification lens element 256. According to this embodiment the magnification lens element 256 provides suitable magnification of the target image, thereby enabling viewing of the target without requiring the user to place their eye in close contact with an eyepiece. Using the herein described optical system 240, the user or caregiver can view the magnified image of the target at a more comfortable (less intrusive) distance from the instrument/patient.

Figure 12:
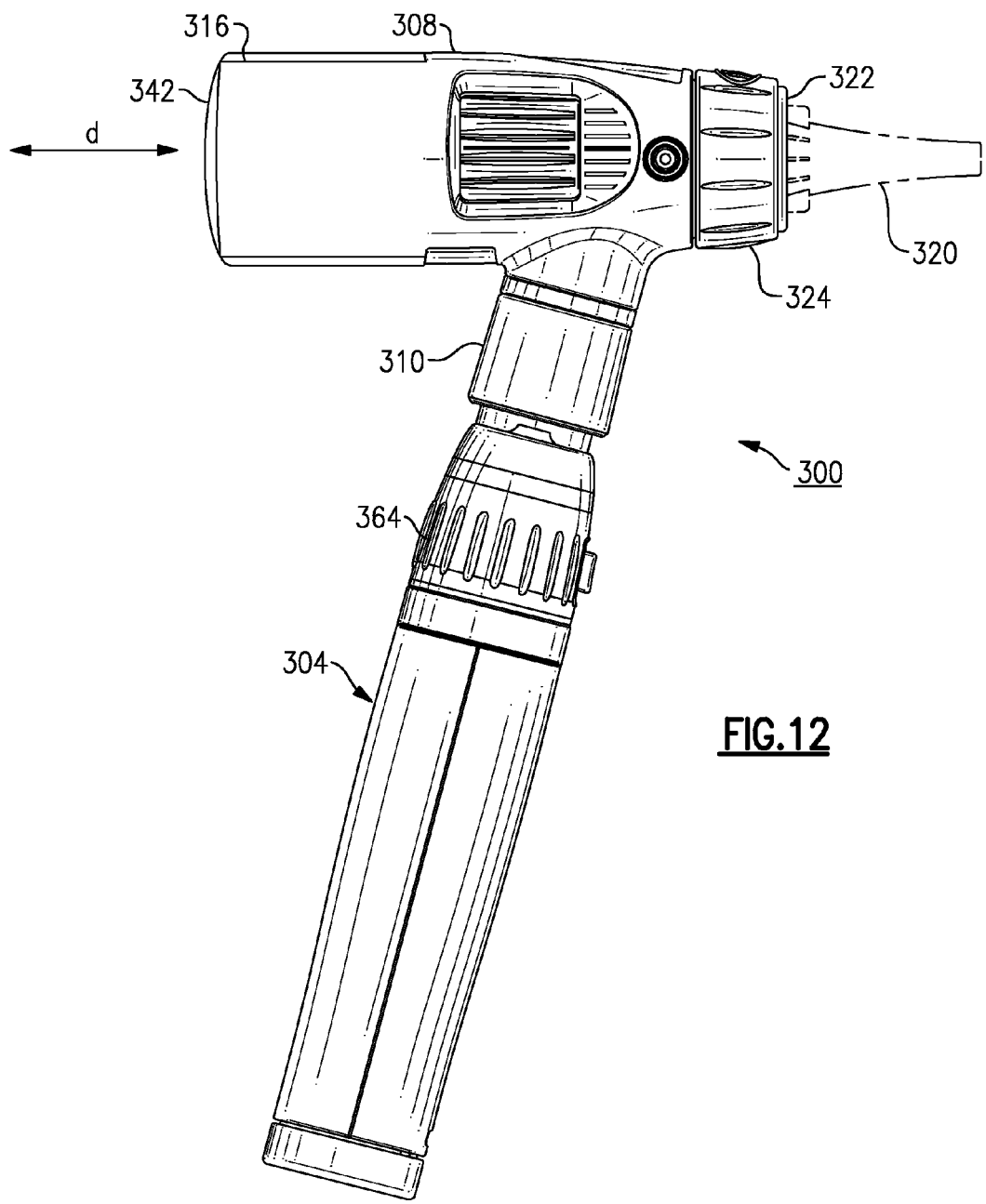
FIG. 12 is a side view of a medical diagnostic instrument in accordance with a second embodiment.
Figure 13:
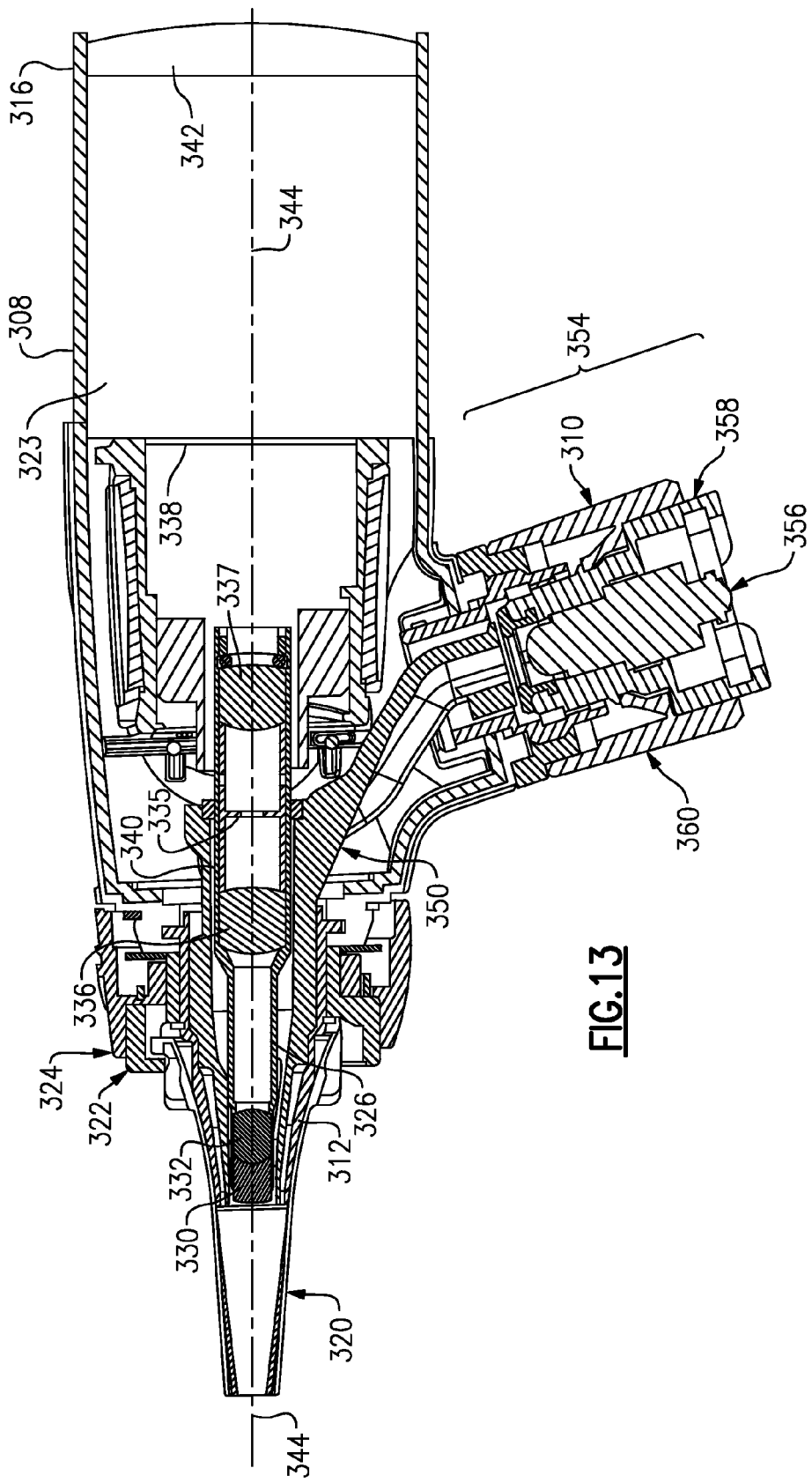
FIG. 13 is a side sectioned elevational view of the medical diagnostic instrument of FIG. 12.

Referring now to FIGS. 12 and 13, there is shown another medical diagnostic instrument and more specifically an otoscope 300 somewhat similar to that previously described in FIGS. 3-9, including a handle 304 and an instrument head 308, the latter being secured to an intermediate necked portion 310 that is provided between the upper end of the handle and the lower end of the instrument head 308. As more clearly shown in FIG. 13, the instrument head 308 is defined by a substantially hollow interior so as to retain a number of components and is defined by a distal axisymmetric insertion portion 312 and an opposing proximal end 316. The distal insertion portion 312 is substantially frusto-conical in configuration and sized to accommodate an axisymmetric hollow speculum tip element 320 in overlaying relation. According to this version and similar to the preceding, the instrument 300 includes a tip actuator mechanism in the instrument head 308 that includes a retainer member 322 having a plurality of annular securing slots (not shown) disposed on a distal facing side thereof, as well as a rotatable actuator knob 324 including a pin feature (not shown) that enables the speculum tip element 320 to be securably retained on the instrument head 308 and selectively released, as needed. Further details relating to the design of the speculum tip element 320, as well as the tip actuator mechanism, are provided in the previously cross-referenced U.S. Pat. No. 7,399,275 B2.

As noted, the herein described instrument head 308 is defined by a substantially hollow interior 323 that is sized and configured to retain an optical system 326. In this embodiment, a first optical doublet includes an objective lens 330 and a second adjacent lens 332. These lenses are retained within a tubular member 340, as well as a pair of relay lenses 336, 337 sandwiched about an aperture stop 335. Each of the foregoing optical elements are arranged along an optical axis/viewing axis 344 of the instrument 300.

Still referring to FIGS. 12 and 13, and in lieu of having an eyepiece mechanism, a focusing screen 338 is fixedly secured and disposed along the optical/viewing axis 344. In one version, the focusing screen 338 can be part of an optical tube assembly (not shown) that is common with the lenses 244, 248. In an alternative version, the focusing screen 338 can be independently movable relative to the lenses 244, 248, therein providing a user-setting diopter adjustment feature. In at least one other version, a focusing mechanism such as described in cross-referenced U.S. Pat. No. 7,399,275 B2 can be employed in regard to the focusing screen and optical system 240 to provide adjustability.

The focusing screen 338 is a section that is made from a suitable material such as ground glass or a section of formed optically transmissive plastic and is disposed at the focal plane of the optical system. At least one magnifying lens element 342 is disposed along the optical axis 344 proximally in relation to the focusing screen 338. According to the described embodiment, a magnifying lens element 342 is positioned within a cavity at the proximal end 316 of the instrument head 308.

An illumination assembly 354 is included within the necked portion 310 of the instrument 300 including an illumination source 356, such as a miniature incandescent lamp retained within a base 358 and further disposed within a cylindrical sleeve member 360. An optical fiber bundle (not shown) is used to direct light from the miniature lamp 356 or other suitable illumination source 356, such as at least one LED, to the distal end of the insertion portion 312.

The tubular member 340 is retained within an inner former assembly 350 within the confines of the instrument head 308 and is fixedly retained from movement therein.

In operation, the instrument 300 releasably receives a disposable speculum tip element 320 in overlaying relation onto the distal axisymmetric insertion portion 312 of the instrument head, in a manner previously discussed. The speculum tip element 320 is sized to prevent insertion beyond a predetermined distance into the ear canal of a patient. The illumination source 356 is then energized, such as through variable control using a rheostat 364 located on the handle 304 of the instrument 300, as emitted light is guided from the illumination assembly 354 to the distal end of the insertion portion 312 of the instrument head 308, permitting visualization of the target area in which a image of the target plane (tympanic membrane) is received by the objective lens 330 and is transmitted along the optical axis 344 to the focusing screen 338 and adjacent magnifying lens element 342. As a result, the user is enabled to view the resulting image of the target area without having to place the eye in close proximity with an eyepiece of the herein described instrument 300.

As previously noted a focusing mechanism, such as described in previously cross referenced U.S. Pat. No. 7,399,275 B2, can also be employed to selectively move the focusing screen 338 and magnifying lens element 342 relative to the remaining optical elements, the mechanism enabling axial movement of each of the foregoing components along the optical axis 344.

PARTS LIST FOR FIGS. 1-13

15 otoscope
16 handle
17 button
18 rheostat
19 incandescent light bulb
20 necked portion, intermediate
21 instrument head
22 insertion portion
26 interior
27 distal end, insertion portion
28 optical fiber bundle
29 proximal end, fiber bundle
30 speculum tip element
30(a) distal end, tip element
31 slot, exterior
34 opening or cavity
35 eyepiece
37 eye
44 insufflation port
60 otoscope
64 instrument head
66 insufflation port
67 windows
68 speculum tip element
70 distal insertion portion
82 retaining member
86 actuator knob
87 inner former assembly
90 optical system
92 optical axis
94 imaging lens train
98 tubular member
100 eyepiece mechanism
102 first axial section
106 second axial section
110 third axial section
112 objective lens
115 seal
116 lens
117 first relay lens
120 aperture stop
124 second relay lens
130 illumination assembly
134 necked portion
136 miniature incandescent bulb
138 base
140 cylindrical sleeve member
144 lens carrier member
145 external threads
146 square distal end, sleeve member
149 threaded portion
151 threaded portion
154 lens retainer member
156 lens
158 lens
160 wave spring
164 lens retainer
166 spacer
168 O-ring
170 sleeve member
171 threads, sleeve member
172 soft grippable elastomeric cover
173 protrusion
175 ball
176 focusing knob
177 compression spring
179 focus position, indicator, cover
180 optical system
181 focus position, indicator, window
182 optical axis
184 objective lens
186 target plane
188 lens
190 focusing screen
194 magnification lens element
195 viewer
200 instrument, otoscopic
204 instrument head
212 necked portion, intermediate
216 illumination source
220 distal axisymmetric insertion portion
224 interior
225 distal opening, insertion portion
228 optical fibers, plurality
229 proximal end, instrument head
232 proximal end, fibers
240 optical system
242 optical axis 244 objective lens
248 second lens
252 focusing screen
256 magnifying lens element
300 otoscope
304 handle
308 instrument head
310 intermediate necked portion
312 distal axisymmetric insertion portion
316 proximal end, instrument head
320 speculum tip element
322 retainer member
323 hollow interior
324 actuator knob
326 optical system
330 lens, objective
332 lens
335 aperture plate/stop
336 relay lens
337 relay lens
338 focusing screen
340 tubular member
342 magnifying lens element
344 optical /viewing axis
350 inner former assembly
354 illumination assembly
356 illumination source
358 base
360 cylindrical sleeve member
364 rheostat It will be readily apparent that there are certain modifications and/or variations which will be readily apparent to one of sufficient skill in accordance with the inventive aspects discussed herein, and further in accordance with the following claims.

The invention claimed is:

1. An otoscope for conducting examinations of the ear, said otoscope comprising:
   an instrument head having an interior and a rear end;
   an optical system comprising at least two lens elements aligned along an optical axis for receiving an image from the ear of the a patient; and
   a focusing screen aligned along said optical axis and disposed at a focal plane of the optical system, the focusing screen being a flat section having no optical power and made from at least one of a light transmissive plastic or ground glass, wherein the focusing screen receives a focused image from said optical system, each of said optical system and said focusing screen being disposed within the interior of said instrument head, wherein said focusing screen presents the focused image to a user at a predetermined distance from the rear end of said instrument head without requiring close proximity between an eye of the user and the rear end of the instrument head.

2. An otoscope as recited in claim 1, further comprising at least one magnification lens element disposed proximally from said focusing screen and aligned along said optical axis.

3. An otoscope as recited in claim 2, wherein said at least one magnification lens element is attachable to the rear end of said instrument head.

4. An otoscope as recited in claim 2, wherein said at least one magnification lens element is releasably attachable to said instrument head.

5. An otoscope as recited in claim 1, further comprising a focusing mechanism for selectively adjusting the focusing position of at least one optical component of said otoscope.

6. An otoscope as recited in claim 5, wherein said focusing mechanism is configured to shift the position of said focusing screen to one of a plurality of focusing positions.

7. An otoscope as recited in claim 5, wherein said focusing mechanism comprises a rotary member disposed on said instrument head, said rotary member being operatively connected to lens tubes containing said at least two lens elements of said optical system, enabling at least one lens tube to be axially displaced relative to at least one adjacent lens tube.

8. An otoscope as recited in claim 1, further comprising a distal insertion portion that receives an axisymmetric tip element for insertion a predetermined distance into the ear canal of a patient, at least one of said at least two lens elements being disposed within said distal insertion portion, said optical system defining an entrance pupil proximal to the distal end of said tip element and distal relative to a distal most lens element of said optical system to permit an entire tympanic membrane of a patient to be captured all at once by said optical system for focusing onto said focusing screen.

9. An otoscope as recited in claim 1, further comprising an illumination source.

10. A portable diagnostic instrument that enables optical viewing of a medical area, said instrument comprising:
    an instrument housing having an interior, a front end, and a rear end;
    an optical system disposed within the interior of said instrument housing, said optical system comprising at least two lens elements aligned along an optical axis; and
    a focusing screen aligned along said optical axis within said instrument housing for focusing an image of the target area received from said optical system, said focusing screen being a flat section having no optical power and made from at least one of a light transmissive plastic or ground glass, the focusing screen being disposed within the interior of said instrument housing and configured to enable a user to effectively view the target area at a predetermined distance away from said instrument housing without requiring close proximity between an eye of the user and the rear end of the instrument housing.

11. An instrument as recited in claim 10, wherein the optical system further comprises at least one magnification lens aligned along said optical axis and proximally relative to said focusing screen.

12. An instrument as recited in claim 11, wherein said at least one magnification lens is attachable to the rear end of said instrument housing.

13. An instrument as recited in claim 10, wherein said instrument is selected from one of the group consisting of an otoscope, a vagiscope, an anoscope, a skin surface microscope, a rhinoscope and an ophthalmoscope.

14. An instrument as recited in claim 13, wherein the instrument is an otoscope comprising a distal insertion portion that receives an axisymmetric tip element for insertion a predetermined distance into the ear canal of a patient, at least one of said at least two lens elements being disposed within said distal insertion portion, the optical system defining an entrance pupil proximal to a distal end of said tip element and distal relative to a distal most lens element of said optical system to permit an entire tympanic membrane of a patient to be captured all at once by said optical system for focusing onto said focusing screen.

15. An instrument as recited in claim 10, further comprising a focusing mechanism for selectively changing the relative position of at least one optical component of said instrument.

16. An instrument as recited in claim 15, wherein said focusing mechanism is configured to move the focusing screen to one of a plurality of axial positions.

17. An instrument as recited in claim 10, further including an illumination source.

* * * * *